(12) United States Patent
Mackie et al.

(10) Patent No.: US 8,076,657 B2
(45) Date of Patent: Dec. 13, 2011

(54) ION RADIATION THERAPY SYSTEM HAVING MAGNETIC FAN BEAM FORMER

(75) Inventors: Thomas R. Mackie, Verona, WI (US); David C. Westerly, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 303 days.

(21) Appl. No.: 12/439,390

(22) PCT Filed: Feb. 27, 2008

(86) PCT No.: PCT/US2008/055083
§ 371 (c)(1),
(2), (4) Date: Feb. 27, 2009

(87) PCT Pub. No.: WO2008/106488
PCT Pub. Date: Sep. 4, 2008

(65) Prior Publication Data
US 2009/0200481 A1    Aug. 13, 2009

Related U.S. Application Data

(60) Provisional application No. 60/891,859, filed on Feb. 27, 2007.

(51) Int. Cl.
*A61N 5/10* (2006.01)
*A61N 5/01* (2006.01)
*G21K 5/04* (2006.01)
*G21K 5/10* (2006.01)

(52) U.S. Cl. ............ 250/492.3; 250/396 ML; 335/212

(58) Field of Classification Search .......... 250/492.3, 250/396 ML; 335/212
See application file for complete search history.

(56) References Cited

U.S. PATENT DOCUMENTS

| | | | |
|---|---|---|---|
| 2,883,569 A * | 4/1959 | Kaiser et al. | 335/212 |
| 4,276,477 A | 6/1981 | Enge | |
| 4,962,317 A * | 10/1990 | Jason et al. | 250/396 ML |
| 5,317,616 A | 5/1994 | Swerdloff et al. | |
| 5,394,452 A | 2/1995 | Swerdloff et al. | |
| 5,442,675 A | 8/1995 | Swerdloff et al. | |
| 5,528,650 A | 6/1996 | Swerdloff et al. | |
| 5,548,627 A | 8/1996 | Swerdloff et al. | |
| 5,625,663 A | 4/1997 | Swerdloff et al. | |
| 5,661,773 A | 8/1997 | Swerdloff et al. | |
| 5,668,371 A * | 9/1997 | Deasy et al. | 250/505.1 |
| 5,673,300 A | 9/1997 | Reckwerdt et al. | |

(Continued)

FOREIGN PATENT DOCUMENTS
EP    0986070 A    3/2000
(Continued)

OTHER PUBLICATIONS

International Search Report, PCT Application No. PCT/US2008/055104, dated Jul. 17, 2008, ISA/EPO, 2280 HV Rijswijk, NL.

(Continued)

*Primary Examiner* — Jack Berman
(74) *Attorney, Agent, or Firm* — Boyle Fredrickson, S.C.

(57) ABSTRACT

An improved beam forming system for ions used in radiation treatment employs a magnet system of successive quadrupole magnets to convert an ion pencil beam to a fan beam with reduced neutrons production compared with conventional beam spreading techniques using scattering foils.

10 Claims, 8 Drawing Sheets

U.S. PATENT DOCUMENTS

| | | | |
|---|---|---|---|
| 5,724,400 | A | 3/1998 | Swerdloff et al. |
| 5,802,136 | A | 9/1998 | Carol |
| 6,345,114 | B1 | 2/2002 | Mackie et al. |
| 6,385,286 | B1 | 5/2002 | Fitchard et al. |
| 6,438,202 | B1 | 8/2002 | Olivera et al. |
| 6,560,311 | B1 | 5/2003 | Shepherd et al. |
| 6,618,467 | B1 | 9/2003 | Ruchala |
| 6,636,622 | B2 | 10/2003 | Mackie et al. |
| 6,661,870 | B2 | 12/2003 | Kapotoes et al. |
| 6,731,970 | B2 | 5/2004 | Scholssbauer et al. |
| 6,915,005 | B1 | 7/2005 | Ruchala et al. |
| 7,046,831 | B2 | 5/2006 | Ruchala et al. |
| 7,186,986 | B2 | 3/2007 | Hinderer et al. |
| 7,207,715 | B2 | 4/2007 | Yue |
| 7,302,038 | B2 | 11/2007 | Mackie |
| 2002/0136439 | A1 | 9/2002 | Ruchala et al. |
| 2003/0160189 | A1 | 8/2003 | Matsuda |
| 2003/0198319 | A1 | 10/2003 | Toth et al. |
| 2005/0123092 | A1 | 6/2005 | Mistretta et al. |
| 2005/0197564 | A1 | 9/2005 | Dempsy |
| 2006/0226372 | A1 | 10/2006 | Yanagisawa |
| 2006/0285639 | A1 | 12/2006 | Olivera et al. |
| 2007/0029510 | A1 | 2/2007 | Hermann |
| 2007/0036267 | A1 | 2/2007 | Becker et al. |
| 2007/0041494 | A1 | 2/2007 | Ruchala et al. |
| 2007/0041495 | A1 | 2/2007 | Olivera et al. |
| 2007/0041496 | A1 | 2/2007 | Olivera et al. |
| 2007/0041497 | A1 | 2/2007 | Schnarr et al. |
| 2007/0041498 | A1 | 2/2007 | Olivera et al. |
| 2007/0041499 | A1 | 2/2007 | Lu et al. |
| 2007/0041500 | A1 | 2/2007 | Olivera et al. |
| 2007/0043286 | A1 | 2/2007 | Lu et al. |
| 2007/0076846 | A1 | 4/2007 | Ruchala et al. |
| 2007/0104316 | A1 | 5/2007 | Ruchala et al. |
| 2007/0195922 | A1 | 8/2007 | Mackie et al. |
| 2007/0195929 | A1 | 8/2007 | Ruchala et al. |
| 2007/0195930 | A1 | 8/2007 | Kapatoes et al. |
| 2007/0242801 | A1 | 10/2007 | Mackie et al. |

FOREIGN PATENT DOCUMENTS

| | | | |
|---|---|---|---|
| EP | 1045399 | A | 10/2000 |
| JP | 2000 214298 | A | 8/2000 |
| WO | WO02/07817 | A | 1/2002 |
| WO | WO02/41948 | A | 5/2002 |
| WO | WO2005/004168 | A | 1/2005 |
| WO | WO2007/021226 | A | 2/2007 |

OTHER PUBLICATIONS

International Search Report, PCT Application No. PCT/US2008/055070, dated Jul. 17, 2008, ISA/EPO, 2280 HV Rijswijk, NL.

International Search Report, PCT Application No. PCT/US2008/055069, dated Jul. 17, 2008, ISA/EPO, 2280 HV Rijswijk, NL.

International Search Report, PCT Application No. PCT/US2008/055161, dated Jul. 17, 2008, ISA/EPO, 2280 HV Rijswijk, NL.

International Search Report, PCT Application No. PCT/US2008/055083, dated Jul. 17, 2008, ISA/EPO, 2280 HV Rijswijk, NL.

International Search Report, PCT Application No. PCT/US2008/055096 dated Jul. 17, 2008, ISA/EPO, 2280 HV Rijswijk, NL.

International Search Report, PCT Application No. PCT/US2008/055090 dated Jul. 17, 2008, ISA/EPO, 2280 HV Rijswijk, NL.

International Search Report, PCT Application No. PCT/US2008/055147, dated Jul. 25, 2008, ISA/EPO, 2280 HV Rijswijk, NL.

Baumert, BG, et al., Dose conformation of intensity-modulated stereotactic photon beams, proton beams, and intensity-modulated proton beams for intracranial lesions, Int. J. Radiat. Oncol. Biol. Phys., 2005, 60:1314-1324, Elsevier, Amsterdam, Netherlands.

Deasy, Jo, et al., Distal edge tracking: a proposed delivery method for conformal proton therapy using intensity modulation, 1997, pp. 406-409, Proceedings of the XIIth International Congress on Computers in Radiotherapy May 27-30, 1997, Salt Lake City, IEEE Publishing, Los Alamitos, California, USA.

Deasy, Jo, A proton dose calculation algorithm for conformal therapy simulations based on Moliere theory of lateral deflections, Med. Phys., Apr. 1998, 25:476-483, American Association of Physical Medicine, New York, New York.

Lomax, AJ, Intensity modulation methods for proton radiotherapy, Phys. Med. Biol., 1999 44:185-205, IOP Publishing Ltd., Bristol, UK.

Lomax, AJ, et al. Intensity modulated proton therapy: A clinical example, Mar. 2001, Med. Phys. 28:317-324, , American Association of Physical Medicine, New York, New York.

Lomax, AJ, Compensated and intensity-modulated proton therapy, in Palta J, and Mackie TR (eds), Intensity Modulated Radiation Therapy: The State of the Art, Nov. 2004, pp. 787-828, Medical Physics Publishing Madison, WI.

Lomax, AJ, et al., Treatment planning and verification of proton therapy using spot scanning: initial experiences. 2004a, Med. Phys. 31:3150-3157, American Association of Physical Medicine, New York, New York.

Lomax, AJ, et al., The clinical potential of intensity modulated proton therapy, 2004b, Z. Med. Phys. 14:147-152, Elsevier, Amsterdam, Netherlands.

Kanai, T, et al., Spot scanning system for proton radiotherapy, Jul./Aug. 1980, Med. Phys 7:365-369, American Association of Physical Medicine, New York, New York.

Moyers MF, (Proton therapy, Van Dyk (ed), The Modern Technology of Radiation Oncology, 1999, pp. 823-869, Medical Physics Publishing, Madison, WI.

Nill, S, et al., Inverse planning of intensity modulated proton therapy, 2004, Z Med. Phys. 14:35-40, Elsevier, Amsterdam, Netherlands.

Oelfke U, et al., Intensity modulated radiotherapy with charged particle beams: Studies of inverse treatment planning for rotation therapy. Jun. 2000, Med. Phys, 27:1246-1257, American Association of Physical Medicine, New York, New York.

Paganetti H, Proton Therapy: A Workshop Handout. 2005, Private Communication, Massachusetts General Hospital, Boston, MA.

Sampayan S, et al. Development of a compact radiography accelerator using dielectric wall accelerator technology, Jun. 6, 2005, Proceed. Int. Pulsed Power Conf. Monterey, CA, Lawrence Livermore Laboratory, Livermore, CA.

Wilson RW., Radiological use of fast protons. Nov. 1946, Radiology 47:487-491, Radiological Society of North America, Easton, Pennsylvania.

Yu C., Intensity modulated arc therapy with dynamic multileaf collimation: an alternative to tomotherapy, 1995, Phys. Med. Biol. 40:1435-1449, IOP Publishing Ltd., Bristol, UK.

Anferov V., Combined X-Y scanning magnet for conformal proton radiation therapy, Med. Phys. , Mar. 2005, 32:815-818, American Association of Physical Medicine, New York, New York.

Goitein, M., Beam scanning for heavy charged particle radiotherapy, Nov./Dec. 1983, Med. Phys. 10 (6) pp. 831-840, American Association of Physical Medicine, New York, New York.

* cited by examiner

ION RADIATION THERAPY SYSTEM HAVING MAGNETIC FAN BEAM FORMER

CROSS-REFERENCE TO RELATED APPLICATIONS

This application claims the benefit of U.S. Provisional Application 60/891,859, filed Feb. 27, 2007, and PCT Application PCT/US2008/055083, filed Feb. 27, 2008, the disclosures of which are incorporated herein by reference.

STATEMENT REGARDING FEDERALLY SPONSORED RESEARCH OR DEVELOPMENT

This invention was made with United States government support awarded by the following agency: NIH CA088960. The United States government has certain rights in this invention.

BACKGROUND OF THE INVENTION

The present invention relates to radiotherapy systems, such as those using ions like protons, for the treatment of cancer and, in particular, to a system providing improved treatment speed and accuracy.

In external beam radiation therapy, tumors within a patient are treated by directing high-energy radiation in one or more beams toward the tumor. Highly sophisticated external beam radiation systems, for example, as manufactured by Tomo-Therapy Inc., employ intensity modulation techniques to improve the conformity of high dose regions to the tumor volume. With TomoTherapy, a tumor is treated with multiple x-ray fan beams directed at the patient over an angular range of 360°. Each of the beams is comprised of individually modulated rays whose intensities can be controlled so that the combined effect of the rays over the range of angles, is the delivery of highly conformal dose distributions to arbitrarily complex target volumes within the patient.

One of the drawbacks of external beam x-ray therapy is that x-rays irradiate tissue along the entire path of each ray, including healthy tissues both proximal and distal to the tumor volume. While judicious selection of the angles and intensities of the x-ray beams can minimize radiation applied to healthy tissue outside of the tumor, the inevitability with x-rays of irradiating healthy tissue along the path leading to and exiting from the tumor has led to a renewed interest in the use of ions, such as protons, as a substitute for x-rays in radiotherapy.

Unlike x-rays, protons and other charged particles can be range modulated and made to stop within the target volume; thereby eliminating exit dose to healthy tissue on the far side of the tumor. In addition, the dose deposited by a proton beam is not uniform along the path of the beam, but rather rises substantially near the protons end of range in a region known as the "Bragg peak". These two features allow improved concentration of dose within the tumor.

Because the size of the proton beam extracted from a typical proton accelerator is generally too small for the treatment of most disease sites, current proton therapy systems adopt one of two general approaches to treat clinically observed target volumes. In the first approach, termed the "spread out Bragg peak" (SOBP) approach, the range of the distal end of a narrow proton pencil beam (the Bragg peak) is modulated using a spinning propeller of low atomic-number material with blades of varying thickness; allowing for a uniform dose to be delivered to a spread out region in depth. This beam is then broadened laterally using a series of lead scattering foils and shaped using field specific brass collimators. At this point, the depth of penetration of the broadened beam is shaped to conform to the distal side of the target volume from each beam angle using custom-built, 2-D range compensators before finally being delivered to the patient for treatment.

This technique can treat the entire tumor at once and therefore is fast. However, the use of the range modulating wheel makes it difficult to conform the dose to the tumor in regions proximal to the target volume, and the construction of special collimators and compensators are required for each treatment field. In addition, the use of high atomic number scattering foils and collimators result in neutron production—which can contribute unwanted dose to the patient during treatment.

In a second approach, termed the "magnetic spot scanning" (MSS) approach, the narrowly collimated proton "pencil beam" extracted from the proton accelerator is modulated in range and magnetically steered in angle to deposit the dose as a series of small spots within the target volume. The spots are positioned in successive exposures until an arbitrary tumor volume has been irradiated. This approach is potentially very accurate, but because the tumor is treated in many successive exposures, this approach is much slower than the SOBP approach. Furthermore, the use of many small, precisely overlapping beam spots creates the risk of "hot and cold spots" appearing in the target volume due to errors in spot placement. This risk is greatly exacerbated if there is any patient movement between spot exposures.

SUMMARY OF THE INVENTION

The present invention provides a treatment system that employs a fan beam of ions composed of "beamlets", each of which may be separately modulated in both range and intensity. In this way, the present invention combines the benefits of simultaneously treating different portions of the tumor (as with SOBP) with the benefit of having precise control over each individual beamlet (as with MSS). The invention described in this application concerns a method of converting a pencil beam into a fan beam relying entirely on magnetic deflection and does not require scattering foils or the like. Using this method, the production of neutrons—which result in unwanted dose to the patient—is greatly reduced.

Specifically then, the present invention provides an ion therapy machine for the treatment of a patient, with the machine having a treatment head positionable about a patient support (i.e. a treatment couch) for directing a beam of protons or other ions toward the patient over a range of angles. A magnet system within the treatment head receives a pencil beam of ions and spreads them into a fan beam by magnetic deflection.

It is thus one object of one embodiment of the invention to provide for a fan beam of protons or other ions with greatly reduced neutron contamination compared to that obtained using a spreading foil or other conventional scattering materials.

The fan beam may have a cross-sectional width greater than five times that of its cross-sectional thickness.

It is thus an object of one embodiment of the invention to create a fan beam with a aspect ratio that can subtend a large tumor and yet provide high-resolution treatment along the direction normal to the broad face of the fan beam.

The ion therapy machine includes a modulator receiving the fan beam to separately modulate individual beamlets, with beamlets being defined as adjacent sectors of the fan beam.

It is thus an object of one embodiment of the invention to provide a beam shape and size that may be readily modulated to allow sophisticated, simultaneous treatment of different regions of the tumor.

The magnet system may comprise one or more quadrupole magnets positioned successively along an axis of the pencil beam of ions with any successive quadrupole magnets (if any) aligned in the same orientation as the first. The quadrupole magnet(s) may each include two pairs of magnets, magnets of each pair opposed along a magnet axis perpendicular to the axis of the pencil beam of ions, with the two magnet axes perpendicular to each other and with one pair of magnets having opposed north poles and the other pair having opposed south poles.

It is thus an object of one embodiment of the invention to make use of a well-characterized quadrupole magnet structure for the purpose of creating a fan beam.

The invention may further include a means for adjusting the separation of the quadrupole magnets along the axis to change the cross-sectional dimension of the fan beam.

It is thus another object of one embodiment of the invention to permit the size of the fan beam to be adjusted either to conform to a predetermined size with changes in the proton beam characteristic or to allow dynamic changes of the fan beam size as part of the treatment process.

These particular objects and advantages may apply to only some embodiments falling within the claims and thus do not define the scope of the invention.

DETAILED DESCRIPTION OF THE PREFERRED EMBODIMENT

Figure 1:
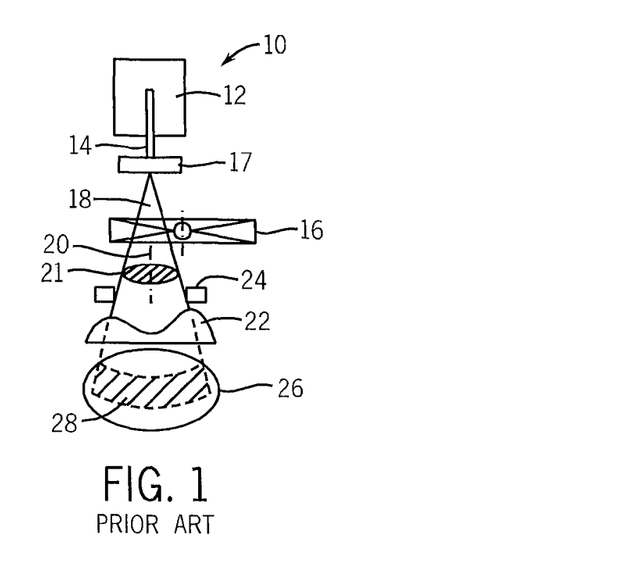
FIG. 1 is a simplified representation of the elements of a prior art radiation therapy system using the SOBP approach described above.

Referring now to FIG. 1, a conventional ion radiation therapy system 10 employing the SOBP approach described above provides an ion source 12 producing a pencil beam 14 of ions traveling along an axis 20.

The pencil beam 14 may be received by a foil 17 scattering the pencil beam into a cone beam 18 having a circular cross-section 21. The energy of the ions in the cone beam 18 is then received by a rotating wedge propeller placing a material of varying thickness in the cone beam 18 and acting as a range shifter 16 continuously changing the energy and thus range of penetration of the ions into tissue.

The cone beam 18 then passes through a collimator 24 approximating the outline of the tumor and a compensator 22 tailor-made for the particular tumor being treated after which the cone beam 18 is received by the patient 26 to produce a treatment pattern 28. As noted, this treatment approach simultaneously treats the entire volume of the tumor and is therefore relatively quick, but requires custom built collimators 24 and compensators 22 and also produces a treatment pattern 28 with imperfect conformance to an arbitrary tumor volume.

Figure 2:
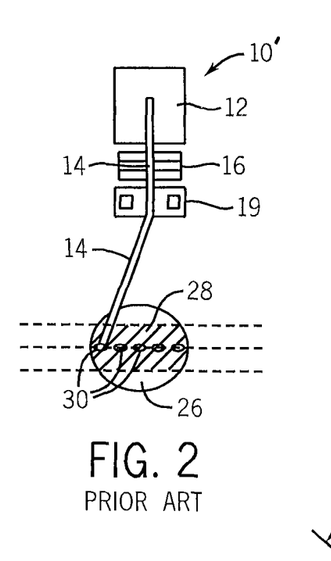
FIG. 2 is a figure similar to that of FIG. 1 showing the elements of a prior art radiation therapy system using the MSS approach described above.

Referring to FIG. 2, a radiation therapy system 10' for implementing the MSS approach, described above, receives a pencil beam 14 from an ion source 12 and passes it through a range shifter 16, for example, a set of movable plastic blocks of different thicknesses. The range shifted pencil beam 14 passes next to a magnetic steering yoke 19 which steers the pencil beam 14 to different spots 30 within the patient 26. Multiple spots 30 together create the treatment pattern 28.

This system produces good conformance of the treatment pattern 28 to an arbitrary tumor, but the sequential process is slow.

Figure 3:
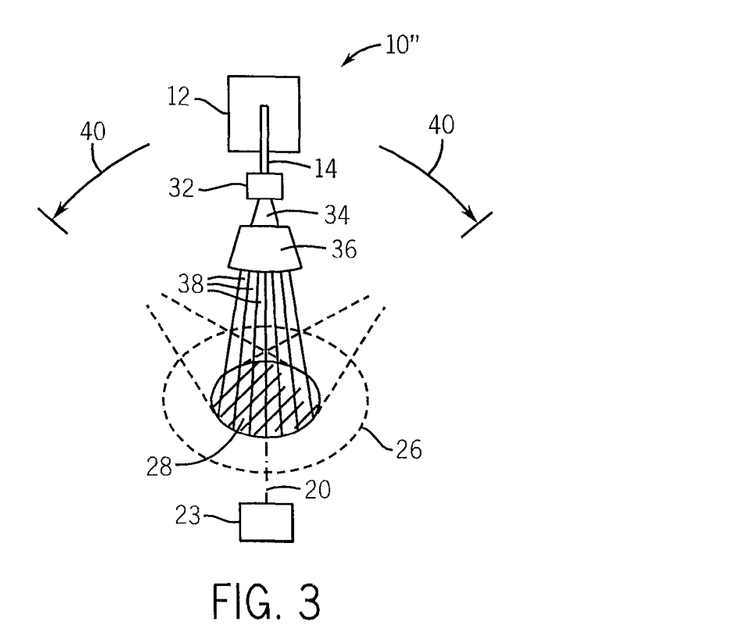
FIG. 3 is a figure similar to that of FIGS. 1 and 2 showing the elements of a fan beam system of the present invention employing a fan beam with individually modulated beamlets and a rocking exposure pattern.

Referring now to FIG. 3, the radiation therapy system 10" of the present invention employs an ion source 12 producing a pencil beam 14. In a preferred embodiment, the pencil beam 14 is received by a magnetic beam former 32 converting the pencil beam 14 into a fan beam 34 by magnetic deflection rather than scattering and thus minimizing the generation of neutrons.

The fan beam 34 is next received by a binary shutter system 36 which individually modulates the range and the intensity of the individual beamlets 38 of the fan beam 34, the beamlets 38 being adjacent sectors of that fan beam 34. The modulated fan beam 34 may be moved in a partial arc 40 with respect to the patient 26 to provide for more complex treatment patterns 28 taking advantage both of multiple angles of treatment and the ability to individually control the intensity and range of the beamlets 38.

Figure 4:
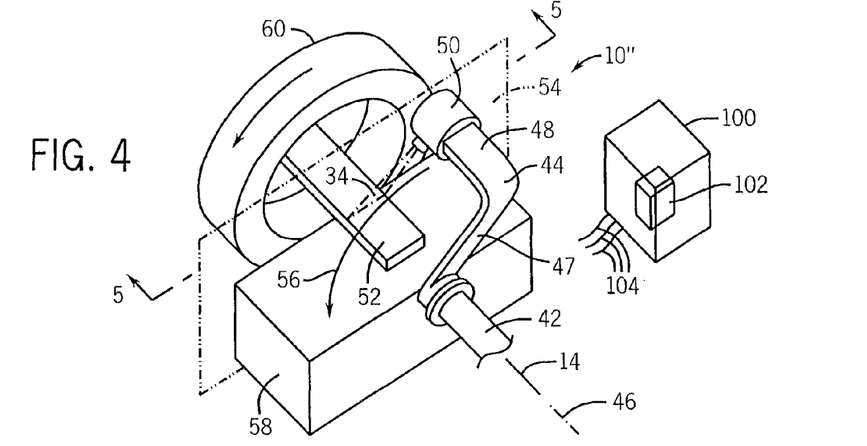
FIG. 4 is a perspective view of an ion therapy machine incorporating the elements of FIG. 3 providing constrained rotation of the fan beam.

Referring now to FIG. 4, the structure of the radiation therapy system 10" may provide, for example, an axial proton beam conduit 42 receiving the pencil beam 14 of protons, for example, from a remote cyclotron or synchrotron (not shown).

Beam steering magnets of a type well known in the art (not shown) may bend to the pencil beam 14 to follow a "crank arm" path of a gantry 44 having a radially extending segment 47 passing on a line of radius from an axis 46 of the entering pencil beam 14 and an axial segment 48 parallel to the axis 46 but spaced from the axis 46 as attached to the end of the radially extending segment 47. The distal end of the axial segment 48 holds a gantry head 50 (whose elements are shown generally in FIG. 3) and which directs a fan beam 34 toward a patient support 52, the latter generally aligned with the axis 46.

The fan beam 34 lies generally within a plane of rotation 54 of the gantry head 50 as the gantry head 50 moves about the patient support 52. By aligning the axis of rotation of the gantry head 50 with the axis 46 of the entering pencil beam 14, constant field bending magnets within the gantry 44 may channel the pencil beam 14 to the gantry head 50 at any of its angular positions.

Figure 5:
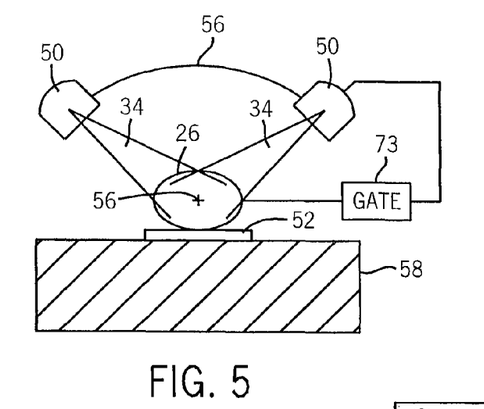
FIG. 5 is a cross-section taken along line 5-5 of FIG. 4 showing the range of motion of a center axis of the fan beam in the present invention with respect to a stationary neutron shield.

Referring momentarily to FIG. 5, the gantry head 50 may rotate in an arc 56 about the axis 46 by an amount substantially less than 180° and in the preferred embodiment approximately 150°. As will be described further below, the present inventors have determined that this limited rotation, un-intuitively, can provide a superior dose pattern 28 when compared to a more complete 360° rotational of the gantry head 50, such as would be preferred for intensity modulated radiation therapy using photons.

The limited range of arc 56 allows a massive stationary neutron stop 58 to be placed under the patient support 52 to receive neutrons generated by interaction of the ions with the patient 26 over the full range of arc 56. The ability to use a stationary neutron stop 58, allows the neutron stop 58 to be larger and closer to the patient 26, allowing, for example, a form in-place concrete neutron shield. Referring now to FIG. 3, optionally, the stationary neutron stop 58 may be supplemented with a movable neutron stop 23 mounted to an extension on the gantry 44 (not shown) to move therewith in opposition to the ion source 12. This movable neutron stop 23 may provide a counterweight for the gantry 44 and may reduce the size of the stationary neutron stop 58.

Figure 6:
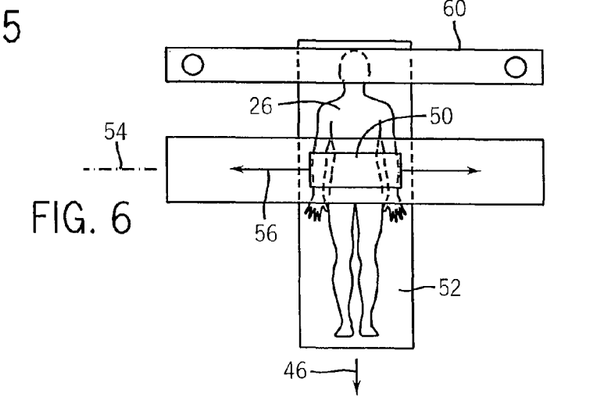
FIG. 6 is a top plan view in phantom of the system of FIG. 5 showing positioning of a patient to be pre-scanned with a tomography ring and then treated using the present invention.

Referring now to FIGS. 4 and 6, an x-ray tomography ring 60 may be placed adjacent to the neutron stop 58 along the axis 46 so as to provide for planning tomographic images of the patient 26 contemporaneous with the radiation treatment. The displacement of the x-ray tomography ring 60 from the plane of rotation 54 allows a full 360° of access to the patient (generally required of an x-ray tomography machine) for supporting both the detector and opposed x-ray source on opposite sides of the patient.

Figure 7A:
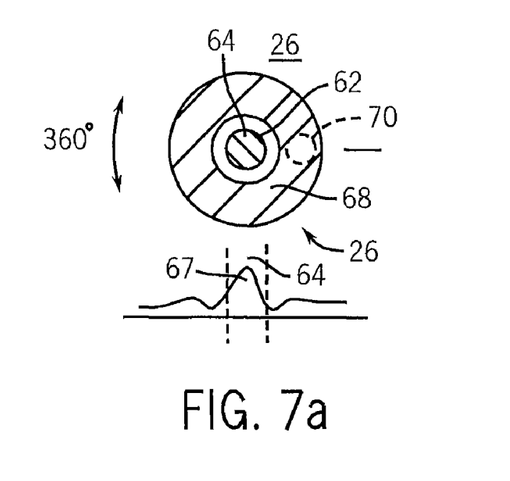
FIGS. 7a and 7b are simplified representations of cross-sectional dose patterns for treatment of a tumor generated with a 360° scan and generated with a 150° scan per one embodiment of the present invention showing the latter scan's superior protection of sensitive distal tissue.
Figure 7B:
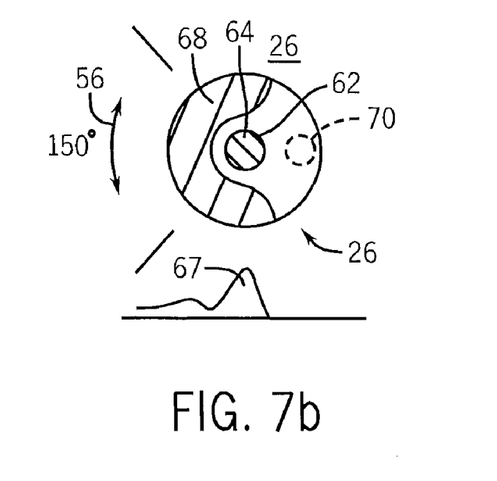

Referring now to FIGS. 7a and 7b, a simplified treatment plan may be developed to treat a tumor 62 in the patient 26 having circular cross-section. Such a plan implemented with ion beam exposure over 360° provides a central region 64 of a dose pattern 28 having a high dose value resulting from aligned Bragg peaks 67 of ion beams entering the patient 26 over a range of angles of 360° about the patient. This central region 64 is surrounded by a fringe 68 resulting from a reduced but measurable entrance dose of these proton beams. This fringe 68 can be problematic if there is radiation sensitive tissue 70, as is often the case, directly adjacent to the tumor 62.

As shown in FIG. 7b, a constrained rotation of the gantry head 50 and hence the fan beam 34 can substantially limit the fringe 68 while preserving good conformity between the central region 64 and the tumor 62. The ability to stop the ions within the target volume at the Bragg peak 67 can wholly spare the radiation sensitive tissue 70. The present inventors have determined that the limitation of the arc 56 to as little as 150° still provides close conformance of the shape of the central region 64 to the tumor 62 with minimization of hot/cold spots.

Figure 8:
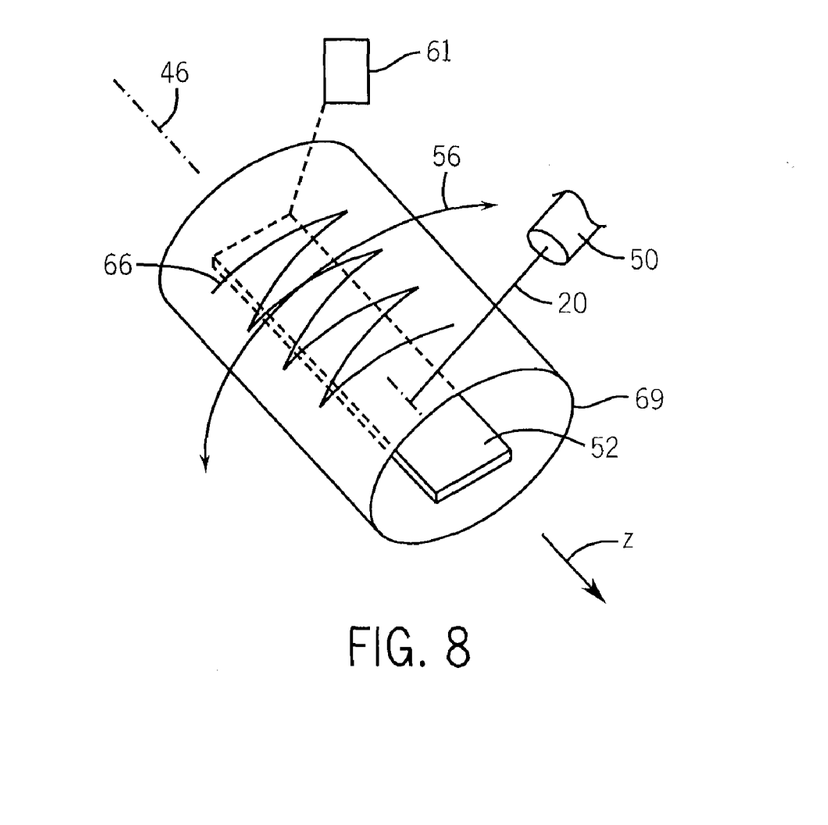
FIG. 8 is a perspective view of a "semi-helical" scanning pattern that may be implemented with the present invention.

Referring now to FIG. 8, the limited width of the fan beam along axes 46 makes it desirable to translate the patient support 52 along axes 46 with respect to the gantry head 50 in order to obtain treatment volumes matching the longitudinal extent of the tumor while still preserving good spatial resolution determined by the thickness of the fan beam. The table may be translated by a table translation mechanism 61 such as a motorized carriage moving the patient support 52 or the gantry head 50 or both.

In one embodiment of the present invention, the translation of the patient support 52 may be continuous as the gantry head 50 rocks back and forth over the treatment arc 56 in a so-called "semi-helical" scan pattern, tracing a sawtooth raster 66 along axes 46 on an imaginary cylinder 69 surrounding the axis 46.

Figure 9:
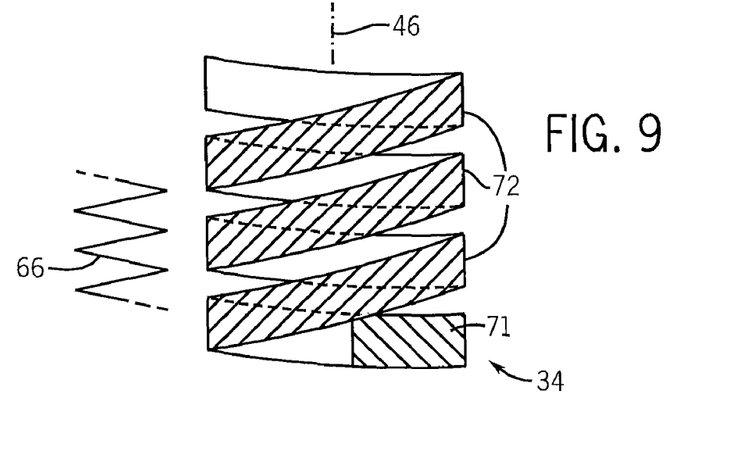
FIG. 9 is a top plan view of the semi-helical scan of FIG. 8 showing overlap of the scans that provides for "re-painting" reducing hot spots/cold spots.

Referring now to FIG. 9, a sweeping of the cross-sectional area 71 of the fan beam 34 in this semi-helical scan pattern may be given a "pitch" by changing the relative speed of movement of the patient support 52 with respect to the speed of movement of the gantry head 50 in each cycle of reciprocation. The pitch determines a degree of overlap between successive sweep paths 72 of the sawtooth raster 66 moving cross-sectional area 71; such overlap serving to reduce hotspots. The pitch shown here is greatly exaggerated and, in practice, would be reduced to a fraction of the width of the cross-sectional area 71 along axes 46. The scanning of the cross-sectional area 71 serves also to eliminate inhomogeneities in the treatment caused by gaps between shutters used to modulate the beamlets 38 as will be described below.

Figure 10:
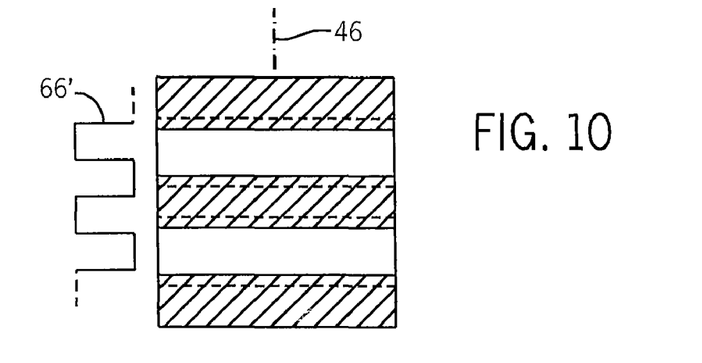
FIG. 10 is a figure similar to that of FIG. 9 showing an alternative rectilinear scan system.

Referring now to FIG. 10, alternatively a rectilinear raster 66' may be adopted where the gantry head 50 is allowed to complete one half of a cycle of its reciprocation about axis 46 and then is stopped at the limits of the arc 56 to allow translation of the patient 26 along axes 46. When movement of the patient 26 is complete the next cycle of reciprocation along arc 56 is performed.

Figure 11:
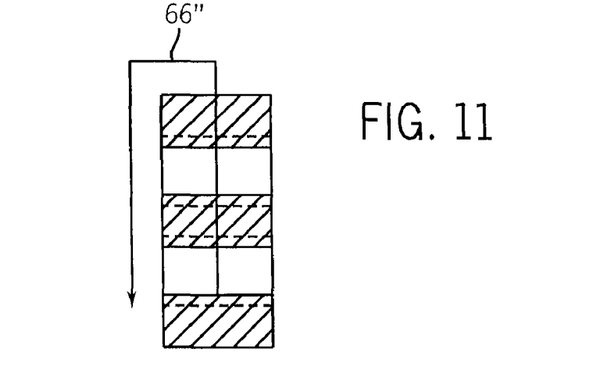
FIG. 11 is a figure similar to that of FIGS. 9 and 10 showing an alternative rectilinear scan that may be superior for motion gating.

Referring now to FIG. 11 and FIG. 5, motion gating may be incorporated into the radiation therapy system 10" of the present invention in which a sensor system 73 senses movement of the patient 26 or internal organs of the patient 26 (for example, using ECG or respiration signals) to turn the fan beam 34 from the gantry head 50 on and off to treat the patient 26 at a constant phase of periodic motion. This gating process may be improved with a rectilinear raster 66" shown in FIG. 11, essentially rotating the rectilinear scanning pattern of FIG. 10 so that a full range of translation of the patient support 52 is completed before moving the gantry head 50 incrementally along arc 56.

Figure 12:
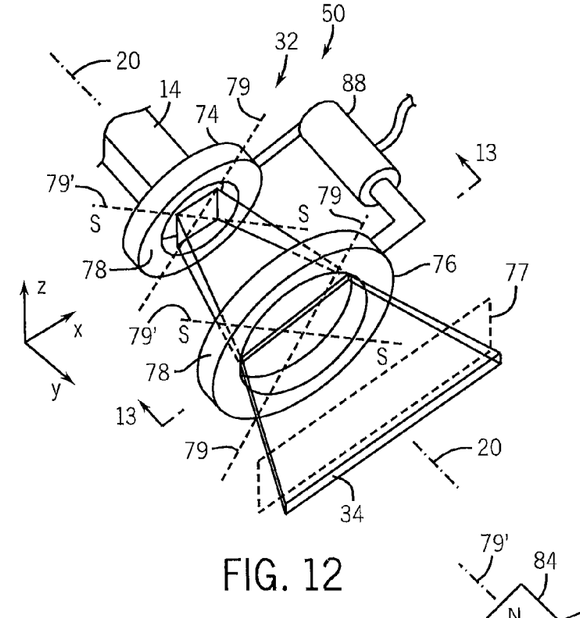
FIG. 12 is a perspective view of a magnetic beam former using two sequential and aligned quadrupole magnets and showing a mechanism for adjusting the separation of those magnets to adjust the resulting fan beam.

Referring now to FIG. 12, the magnetic beam former 32 (shown in FIG. 1) in a preferred embodiment may comprise two quadrupole magnet assemblies 74 and 76 receiving the pencil beam 14 (as delivered to the gantry head 50 along gantry 44). The pencil beam 14 is first received by a first quadrupole magnet assembly 74 and then received by the second quadrupole magnet assembly 76 downstream from the first quadrupole magnet assembly 74. Both quadrupole magnet assemblies 74 and 76 include apertures 78 coaxially aligned along a center axis 20 of the pencil beam 14 and the fan beam 34.

Figure 13:
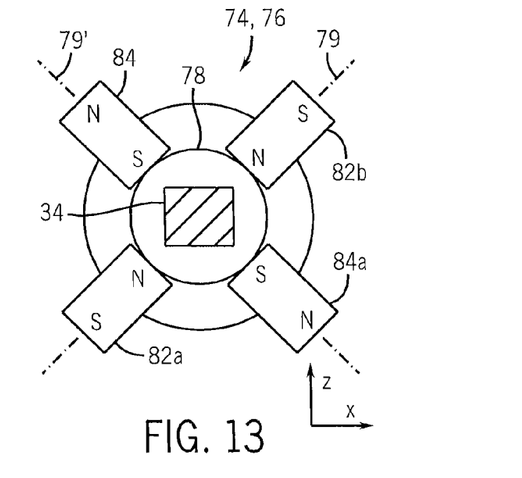
FIG. 13 is a simplified cross-sectional view along 13-13 through one quadrupole magnet of FIG. 12 showing the magnet orientations.
Figure 14:
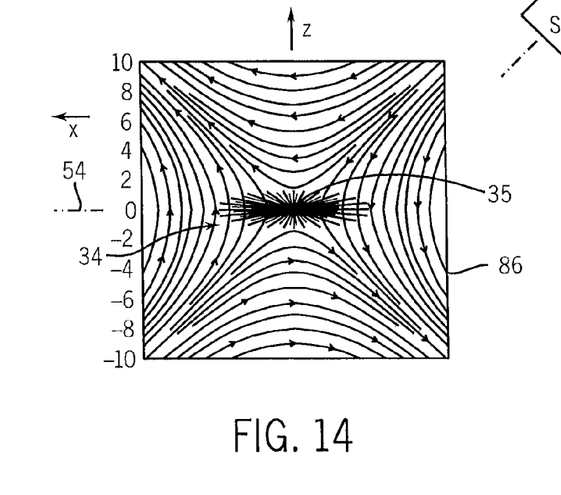
FIG. 14 is a magnetic field map of the quadrupole of FIG. 13.

Referring momentarily to FIGS. 13 and 14, quadrupole magnets of the type used in quadrupole magnet assemblies 74 and 76 are well known in the fields of high-energy accelerator physics and electron microscopy where quadrupole magnets with relative rotations of 90° about the axis of the beam are used to help refocus a pencil beam 14 to maintain its narrow cross-section. Each quadrupole magnet assembly 74 and 76 comprises two pairs of magnets: a first pair 82a and 82b opposed across the aperture 78 along axes 79 with facing north poles, and a second pair 84a and 84b opposed across the aperture 78 along axes 79' perpendicular to axes 79. The magnets may be permanent magnets or preferably electromagnets so that the field strengths may be varied to allow the width and intensity profiles of the resultant fan beam 34 to be varied in both the convergent and divergent planes.

Referring again to FIG. 12, two quadrupole magnet assemblies 74 and 76 are aligned with respect to each other so that axes 79' of quadrupole magnet assembly 74 shares the same orientation as axes 79' of quadrupole magnet assembly 76.

Figure 15:
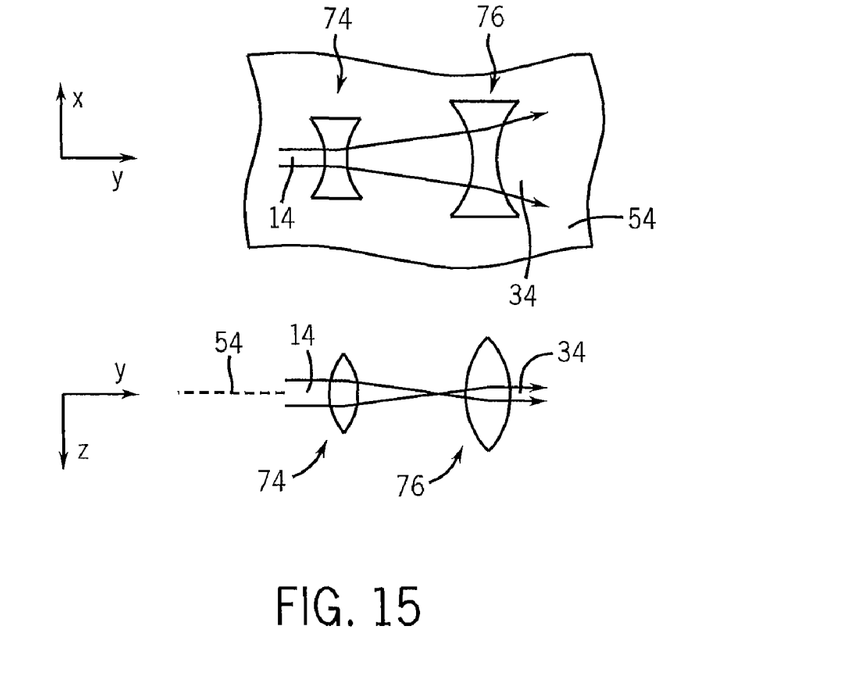
FIG. 15 is an aligned top plan and side elevation view of the beam of FIG. 12 showing the effective operation of two quadrupole magnets as both converging and diverging lenses in different axes.

Referring to FIGS. 6, 14 and 15, the quadrupole magnet assemblies 74 and 76 produce a magnetic field 86 that tends to widen a cross-section 35 of the fan beam 34 along the plane of rotation 54 and compress it in a z-direction normal to the plane of rotation 54.

As shown in FIG. 15, quadrupole magnet assemblies 74 and 76 act like diverging lenses when viewed in the plane of rotation 54 and converging lenses when viewed across the plane of rotation 54. Because the forming of the pencil beam 14 into a fan beam 34 is done without scattering in a solid material, the production of neutrons is greatly reduced.

Note the quadrupole system will work for heavy ions of either polarity with a simple reversal of dimensions.

Referring again to FIG. 12, the quadrupole magnet assemblies 74 and 76 may be connected by controllable actuator mechanism 88 (such as a motor and rack and pinion mechanism) that may separate each of the quadrupole magnet assemblies 74 and 76 along the axis 20 according to an electrical signal and/or by mechanical adjustment. This controllable separation allows adjustment of the cross-sectional dimensions of the fan beam 34 to reduce collimation that also produces neutrons. The adjustment of the fan beam size may also be used for dynamic change of the beamlets 38 during treatment.

Figure 16:
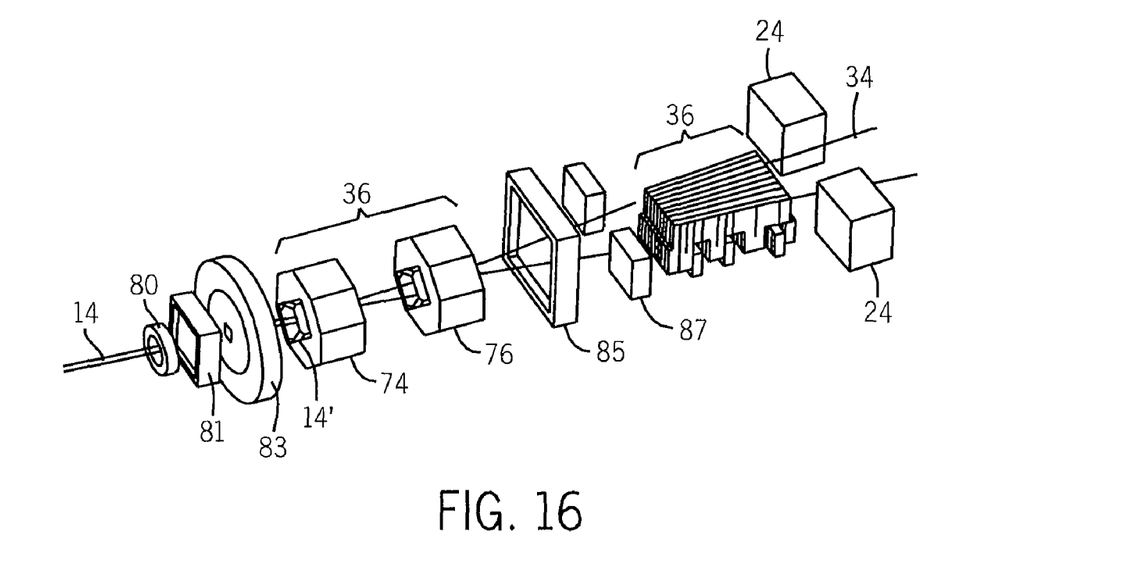
FIG. 16 is a perspective view of the elements of FIG. 3 showing two quadrupole magnets and a binary shutter system that may be used to generate and modulate the fan beam in the present invention.

Referring now to FIG. 16, the pencil beam 14, ultimately received by the magnetic beam former 32 (composed of quadrupole magnet assemblies 74 and 76) may first pass through an emergency beam stop 80 and an entrance dose monitor 81 of conventional design, the latter measuring the energy of the beam 14. A pencil beam aperture collimator 83 may then shape the pencil beam 14 into a predictable cross-section for receipt by quadrupole magnet assembly 74. After exiting from quadrupole magnet assembly 76 the fan beam 34 may pass through a segmented monitor measuring an energy or intensity profile of the beam 34 that may be used to further correct the energy profile of the fan beam 34 (by compensation using the binary shutter system 36 as will be described) or to correct a cross-section of the fan beam 34, for example by controlling the field strengths of electromagnets of the quadrupole magnet assemblies 74 and 76. The fan beam 34 is then received by a set of collimator blocks 87 sharpening the edges of the fan beam to conform with a binary shutter system 36 as will be described below.

Simulations have been performed modeling a 235 MeV proton beam traversing two quadrupole magnet assemblies 74 and 76 having effective lengths of 20 cm and 40 cm with transverse gradients of 22 T/m and 44 T/m respectively and a center-to-center quadrupole separation of 50 cm. The results of these simulations indicate that a proton fan beam of suitable cross-section (40×2 cm2) can be generated from an entrant Gaussian beam of protons (1.5 cm FWHM) over a distance of 1.5 m.

Figure 17:
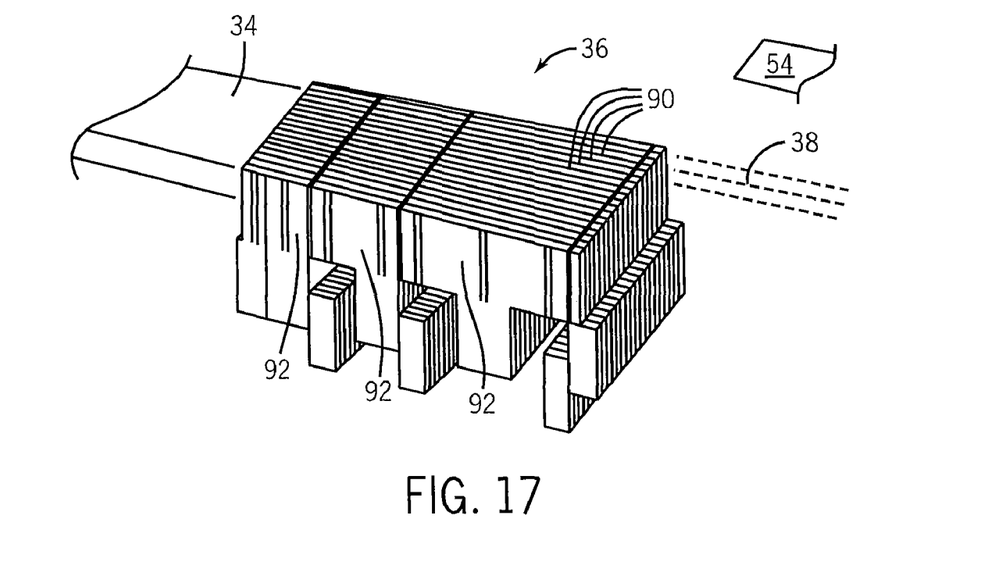
FIG. 17 is a side view of the binary shutter system showing a side-by-side arrangement of arrays of attenuation elements providing shutters.

Referring now to FIGS. 16 and 17, the binary shutter system 36 may provide a set of attenuating arrays 90 each aligned with a separate beamlet 38 of the fan beam 34. Each attenuating array 90 may be composed of a set of attenuating elements 92 (blade) each attenuating element 92 of a single array 90 being aligned with a particular beamlet 38. Multiple arrays 90 are placed side by side to span the width of the fan beam 34 so that each beamlet 38 may be controlled independently by a different array 90.

Figure 18:
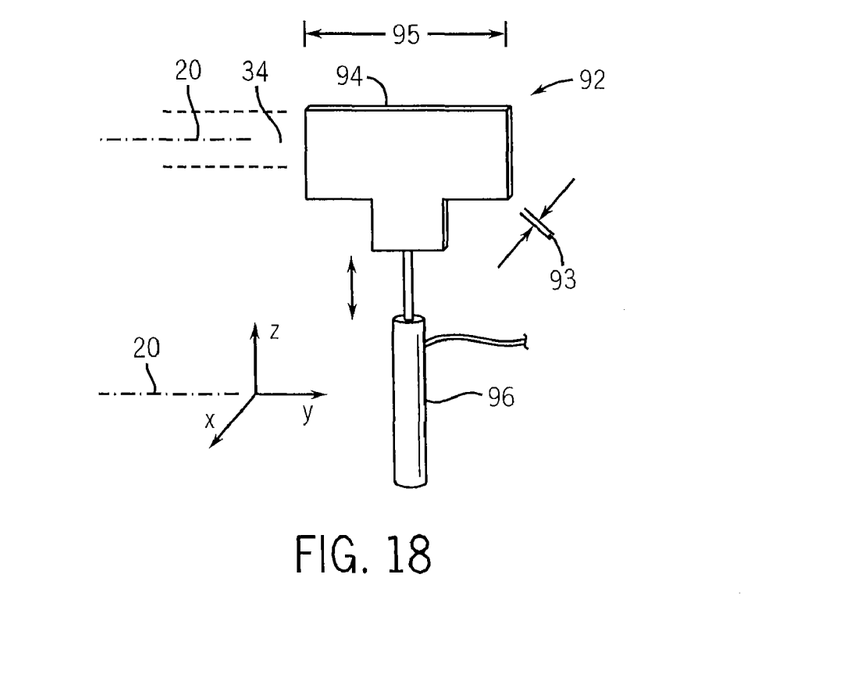
FIG. 18 is a side elevational view of one attenuation element showing its actuator for moving the attenuation element between a retracted position outside of the beam and an extended position within the beam.

Referring now to FIG. 18, each attenuating element 92 comprises a blade 94 of an energy absorbing material having a thickness 93 approximating the angular width of a beamlet within the plane of rotation 54 and a variable length 95 that will differ for different blades 94 as will be described. The blade 94 is attached to an actuator 96 that may move the blade 94 up and down along the y-axis generally perpendicular to the central axis 20 of the fan beam 34. In a preferred embodiment, the blade 94 may be moved between two positions, one within the path of the fan beam 34 and the other completely removed from the path of the fan beam 34. With this "binary" motion the actuator 96 may be extremely simple, for example, a pneumatic piston and cylinder (controlled by fluid pressure controlled in turn by a valve mechanism not shown) or electrical solenoid directly controlled by an electrical circuit.

Figure 19:
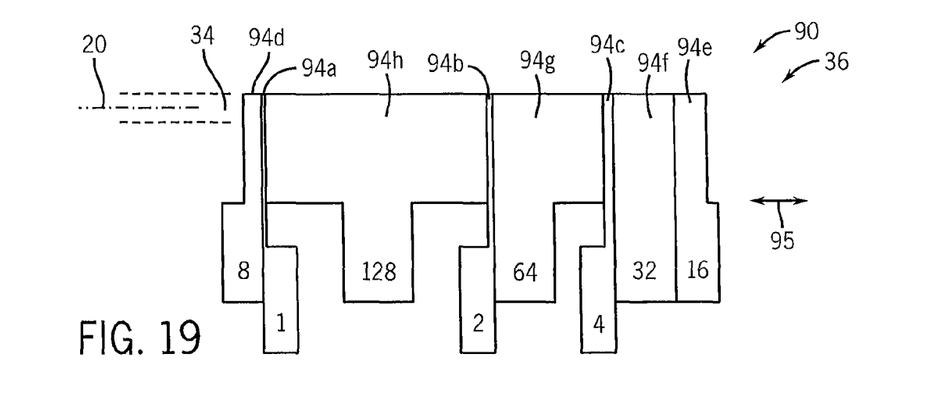
FIG. 19 is a simplified representation of one array of binary-weighted attenuation elements fully extended to block the beam.
Figure 20:
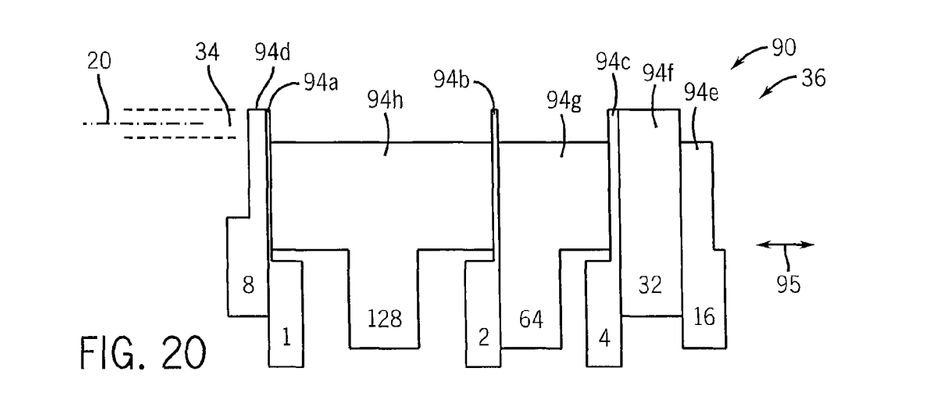
FIG. 20 is a figure similar to that of FIG. 19 showing selected retraction of the attenuation elements such as it may provide controlled energy reduction in the beam.

Referring now to FIG. 19, a single array 90 may, for example, contain eight attenuating elements 92 having blades 94a-94h. In a first embodiment, the length 95 of each blade 94a-94h along axis 20 may be according to a binary power series so, for example, blade 94a through 94h will have relative lengths 95 corresponding to successive terms in a binary power sequence (e.g.: 1, 2, 4, 8, 16 etc.). Thus, for example, blade 94d may be eight times as thick as the thinnest blade 94a. In this way, as shown in FIG. 20, any one of 256 equal increments of attenuation may be obtained by drawing some of the blades 94 out of the beam 34 and placing some of the blades 94 into the beam. In the example of FIG. 20, a relative attenuation of 43 may be obtained consisting of the combined blades 94d, 94a, 94b, and 94f (having attenuation's 8, 1, 2, and 32 respectively where 1 is the attenuation provided by the thinnest blade 94a). This "binary" sequence must be distinguished from the "binary" action of the shutters and a binary sequence need not be used for the binary shutter system 36 as will be described below.

This binary power series provides the simplest blade structure and actuation mechanisms but it will be understood that other power series can also be used and in fact the variations in attenuations among blades 94 need not conform to a power series but, for example, may conform to other series and may include duplicate blades 94 of a single attenuation, for example to operate at higher speed or distribute wear. For example, the blades 94 may have the relative lengths 95 of 1, 1, 3, 6, 9, 18, etc.

Alternatively blades 94 positionable in any of three (or more) positions with respect to the fan beam 34 (and hence capable of providing three effective attenuation levels per attenuating element 92) could be used providing attenuations in the series (0, 1, 2), (0, 3, 9), (0, 9, 18), (0, 27, 54) . . . .

It will be further understood that attenuating elements 92 need not be constructed of a uniform material in which their length 95 corresponds to attenuation, but may be constructed of different materials having different densities to minimize their differences in length 95 for mechanical or structural reasons. The order of the blades 94 in the fan beam 34 need not conform to their relative ranking in attenuation, and in fact in the preferred embodiment this order is buried so as to provide for suitable clearance for the attached actuators 96.

In a preferred embodiment the combination of all attenuating elements 92 completely stops the fan beam 34, and thus a proper selection of different attenuating elements 92 (short of blocking the fan beam 34) may be used to control range shifting of ions of the fan beam 34, while a selection of all attenuating elements 92 (fully blocking the fan beam 34) may be used to control the intensity of the beam through duty-cycle modulation so that both range and intensity may be controlled with the modulator 36. Alternatively a separate blocking element (not shown) for each beamlet 38 may be used to provide this intensity modulation. The intensity modulation or range shifting effected by the binary shutter system 36 may be augmented by other mechanisms applied to some or all of the beamlets 38, for example those correcting the profile of the fan beam 34 or serving to offset the range shifting of all the beamlets 38 based on patient size.

The control of the individual blades 94 may be performed, for example, so that all of the attenuating blades 94 do not move simultaneously but are rather staggered to ensure the minimum deviation in range shifting during the transition of the blades 94. Thus, for example, the movement of blades 94 providing greater attenuation may be alternated with movement of blades 94 providing less attenuation to reduce variations in range shifting.

Figure 21:
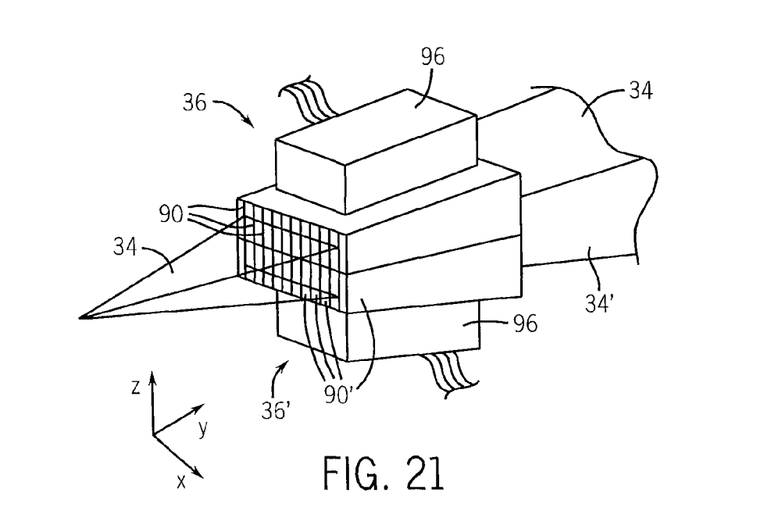
FIG. 21 is an alternative embodiment showing the use of two modulation systems face to face to provide for two independently modulated adjacent fan beams.

Referring now to FIG. 21, two binary shutter system 36 and 36' may be opposed about the fan beam 34 effectively dividing the fan beam 34 along an x-y plane (parallel to the plane of rotation 54) into two separately modulated fan beams 34 and 34' effectively allowing multi-slice treatment of the patient improving the speed/resolution trade-off of the treatment system. In this case the geometry of the actuators 96 and blades 94 allows all of the actuators 96 to be fully displaced out of the area of the beam 34.

The binary shutter system 36 may also be used for photon modulation; the term "radiation" as used herein will include generally both photons and particles serving for treatment of tissue.

Referring again to FIG. 4, an electronic computer 100 executing a stored program may be associated with the radiation therapy system 10" executing a radiation treatment plan that coordinates and controls all of the electrically controllable elements described above including but not limited to the binary shutter system 36, the magnetic beam former 32 (including magnetic field strength of the magnets and their separation) and the movement of the gantry 44 and patient support 52 as well as receipt and control of the x-ray tomography ring 60. This control may be done according to a stored radiation treatment plan, and in light of signals obtained from monitors 81 and 85. Data collected by the computer 100 then provides images, and assessment of the treatment plan, as well as implements feedback loops confirming the proper operation of the system according to techniques known in the art of intensity modulated radiation therapy.

During the movement of the gantry head 50 with respect to the patient support 52, the range and intensity of individual beamlets 38 will be modulated according to a treatment plan stored in the computer 100 and typically determined by a health care professional using an image of the tumor using the tomography ring 60. Determination of the proper modulation of the beamlets 38 may be done by techniques analogous to those used with prior art intensity modulated radiation therapy adapted to the unique properties of ion beams. These techniques include for example Simulated Annealing and gradient based optimization techniques.

The present invention has been described in terms of the preferred embodiment, and it is recognized that equivalents, alternatives, and modifications, aside from those expressly stated, are possible and within the scope of the appending claims.

The invention claimed is:

1. An ion therapy machine for treatment of a patient comprising:
   a treatment head positionable about a patient support for directing a beam of ions toward the patient over a range of angles; and
   a magnet system providing at least two quadrupole magnets within the treatment head receiving a pencil beam of ions and spreading them into a fan beam by magnetic deflection, the quadrupole magnets positioned successively along an axis of the pencil beam and aligned to provide divergence of the pencil beam along a common divergence plane;
   whereby the production of excess neutrons from a beam spreading foil is avoided.

2. The ion therapy machine of claim 1 wherein the fan beam has a cross-sectional width at least 5 times that of its cross-sectional thickness.

3. The ion therapy machine of claim 2 including a modulator receiving the fan beam to separately modulate beamlets, the beamlets being adjacent sectors of the fan beam.

4. The ion therapy machine of claim 1 wherein the quadrupole magnets each comprises two pairs of magnets, with the magnets of each pair opposed along a magnet axis perpendicular to the axis of the pencil beam of ions, with the magnet axes perpendicular to each other, and with one pair having opposed north poles and the other pair having opposed south poles.

5. The heavy ion therapy machine of claim 1 further including an adjustment mechanism to adjust a separation the at least two quadrupole magnets to change at least one of a width and thickness of a cross-section of the fan beam during treatment of a patient.

6. An ion therapy machine for treatment of a patient comprising:
   a treatment head positionable about a patient support for directing a beam of ions toward the patient over a range of angles; and
   a magnet system within the treatment head receiving a pencil beam of ions and spreading them into a fan beam by magnetic deflection, wherein the magnet system comprises at least at least two quadrupole magnets positioned successively along an axis of the pencil beam of ions with two quadrupole magnets having substantially aligned magnetic axes; and a means for adjusting a separation of the pair of quadrupole magnets along the axis to change a cross-sectional dimension of the fan beam;

whereby the production of excess neutrons from beam spreading foils is avoided.

7. A method of treating a patient with a beam of ions comprising:
(a) generating a pencil beam of ions;
(b) receiving the beam of ions with at least two quadrupole magnets aligned to each spread the pencil beam into a fan beam by magnetic deflection in a common plane, the fan beam's largest cross-sectional axis extending along a plane; and
(c) directing the fan beam at a patient at a variety of angles within the plane about the patient.

8. The method of claim 7 wherein the at least two quadrupole magnets are configured to spread the beam into a fan beam having a cross-sectional width at least 5 times that of its cross-sectional thickness.

9. The method of claim 7 further including the step of separately modulating the ions in beamlets being adjacent sectors of the fan beam.

10. A method of treating a patient with a beam of ions comprising:
(a) generating a pencil beam of ions;
(b) receiving the beam of ions with a magnet system to spread the pencil beam into a fan beam by magnetic deflection, the fan beam's largest cross-sectional axis extending along a plane; wherein the magnet system comprises a pair of quadrupole magnets positioned successively along an axis of the pencil beam of ions with each quadrupole magnet rotated 0° about the axis with respect to the others and further including the step of dynamically changing a separation of the quadrupole magnets to change the cross-section of the fan beam during treatment; and
(c) directing the fan beam at a patient at a variety of angles within the plane about the patient.

* * * * *